United States Patent [19]
Gordon et al.

[11] Patent Number: 6,068,640
[45] Date of Patent: May 30, 2000

[54] REMOVAL OF CORNEAL EPITHELIUM

[75] Inventors: Eugene Irving Gordon, Mountainside; Parid Turdiu, West New York, both of N.J.

[73] Assignee: Medjet Inc., Edison, N.J.

[21] Appl. No.: 09/032,324

[22] Filed: Feb. 27, 1998

Related U.S. Application Data

[60] Provisional application No. 60/039,231, Feb. 28, 1997.

[51] Int. Cl.$^7$ ....................................................... A61F 9/00
[52] U.S. Cl. ........................... 606/166; 606/107; 604/294
[58] Field of Search ..................................... 606/107, 131, 606/159, 161, 166; 604/22, 289, 290, 294, 68, 70, 72; 600/401; 239/1, 11, 591, 590, 578; 128/173 H

[56] References Cited

U.S. PATENT DOCUMENTS

| | | | |
|---|---|---|---|
| 3,057,349 | 10/1962 | Ismach | 604/71 |
| 3,818,913 | 6/1974 | Wallach | 128/305 |
| 5,026,343 | 6/1991 | Holzer | 604/68 |
| 5,556,406 | 9/1996 | Gordon et al. | 606/166 |
| 5,833,701 | 11/1998 | Gordon | 606/166 |
| 5,861,955 | 1/1999 | Gordon | 356/360 |
| 5,899,880 | 5/1999 | Bellhouse et al. | 604/70 |

*Primary Examiner*—Wynn Wood Coggins
*Assistant Examiner*—Jennifer Maynard
*Attorney, Agent, or Firm*—Graham & James LLP

[57] ABSTRACT

A method and device for the clean, non-traumatic removal of a diseased or otherwise eroded, cut, damaged, or dystrophied epithelium layer from the cornea of an eye, for the enhanced regeneration thereof or as the first step in a PRK procedure. The device includes a source for high speed, water-jet with sufficient speed and pressure to cleanly remove the epithelium layer from the Bowman's layer but at a speed which does not affect the harder, underlying Bowman's layer. The device further includes a preferably flat, impinging surface adapted to be directly placed on the epithelium with a laterally extending portion. The flat surface lightly applanates the cornea. The waterjet is adapted to impinge on the flat surface whereby the surface causes the waterjet to laterally radiate and continuously "brush" off the epithelium until the Bowman's layer is reached. Continued waterjet impingement, for a limited period thereafter, does not affect the Bowman's layer and merely harmlessly irrigates the eye.

9 Claims, 2 Drawing Sheets

FIG.1
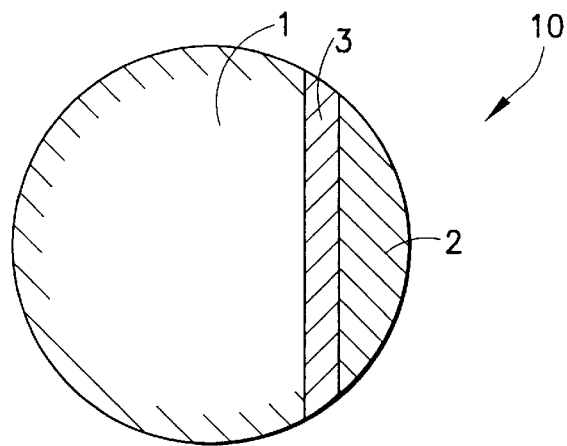
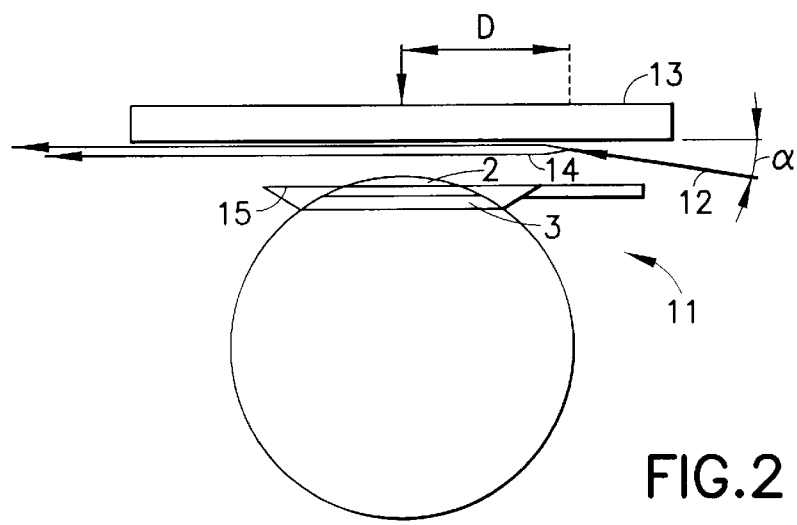
FIG.2
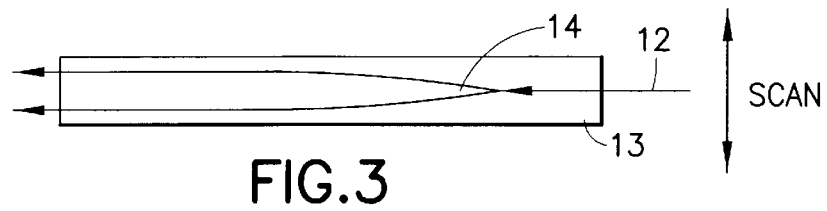
FIG.3

REMOVAL OF CORNEAL EPITHELIUM

This application is based on provisional application No. 60/039,231 filed Feb. 28, 1997, and takes priority therefrom.

FIELD OF THE INVENTION

This invention relates to methods and devices utilized in surgical procedures for the cornea and particularly to those procedures involving removal of corneal epithelium tissue to effect such treatments.

BACKGROUND OF THE INVENTION

The cornea comprises a thin protective surface epithelium layer, typically a circular area of about 10 mm in diameter, on top of the Bowman's membrane or layer, which in turn covers the major corneal stroma. Although the epithelium has no blood cells it does have nerve cell endings. When the corneal epithelium is eroded, cut, damaged, dystrophied or diseased, it can be removed and it will regenerate in about 2–3 days. The epithelium is also removed as a precursor to laser refractive surgery of using a laser over a circular area of a diameter somewhat larger than 6 mm.

While the epithelium is regenerative, the underlying Bowman's membrane is not. With ablative corneal tissue removal procedures, such as PRK (photo-refractive keratectomy, an ablative procedure using an excimer laser-based system), the epithelium and Bowman's membrane are removed together with a portion of the stroma. As soon as the epithelium is removed as the first step in the PRK procedure the cornea at first dehydrates and the begins to hydrate which changes the ablation rate for PRK and the thickness of the cornea and the amount of material actually removed become uncertain. In addition, the longer the time period for epithelium removal, the greater the uncertainty with respect to the degree of hydration and the greater the inaccuracy of the PRK. In addition, debris may locally block or mask photo ablation with formation of isolated central islands of unremoved materials.

After removal, the epithelium regenerates on the exposed outer surface of the cornea either on the Bowman's layer or directly on the stroma, if the Bowman's layer has been removed, since the Bowman's layer is not regenerated. Direct regrowth of the epithelium on the stroma can however cause an undesirable corneal haze which gradually dissipates over time.

Removal of the epithelium alone, if necessary, is usually generally accomplished by means of scraping with a surgical blade. However, this is a rough, imperfect, and inaccurate means for removal of the epithelium and its use tends to damage the underlying Bowman's layer. Blade scraping is also slow and tedious and requires about a minute or more to remove the epithelium. Because of the scraping, the new surface of the anterior surface of the Bowman's layer, has substantial debris and is usually badly damaged. Evidence of such damage is readily ascertained by viewing under high magnification scanning electron microscope which shows that the new exposed surface does not exhibit the typical honeycomb appearance of the Bowman's layer.

Solvent removal of the epithelium is the most efficacious method for removal, without physical damage to the Bowman's layer and over a well defined area. Thus, a solvent such as alcohol is capable of cleanly dissolving away the epithelium. However, alcohol and other similar solvents are toxic and cannot be safely used on live eyes.

A new procedure has been developed for removal of the epithelium layer wherein a circular, rotating brush is pressed against the epithelium to quickly wear the epithelium away. The extent of damage this causes to the Bowman's layer is similar to that of the blade and it appears that the procedure is operator dependent with the amount of damage to the Bowman's layer being related to the degree of engagement pressure between brush and cornea as exerted by the operator.

The PRK system is also capable of removing epithelium. However, the epithelium is generally not of uniform thickness and it is not possible to remove all of the epithelium without removing some of the Bowman's layer.

SUMMARY OF THE INVENTION

It is therefore the object of the present invention to provide a method and device for the clean, brush-like removal of the epithelium surface layer of the cornea with no damage to the underlying Bowman's layer.

It is a further object of the present invention to provide such method and device wherein the epithelium layer is cleanly removed in no more than a few seconds without being subject to detrimental operator variations.

Generally the present invention comprises a method and device for removal of the epithelium surface layer on the cornea with no damage to the underlying Bowman's layer. The method and device are operatively based on the difference in physical characteristics of the epithelium and Bowman's layers, wherein the latter is slightly harder and more physically resistant than the former. However, this variation is not a normal factor in tissue removal since physical control of this minute magnitude of difference, with an operator dependent surgical blade or brush, is not viable, nor is effective discriminatory heat control of an ablative laser. In fact, with the laser, it is more difficult to remove the epithelium than to remove the Bowman's layer.

In accordance with the present invention effective discriminatory force means is applied to the epithelium layer wherein the means operates in the force "window" between a force sufficient to remove epithelium tissue up to but not including a force sufficient to damage or remove Bowman's layer tissue. A force means controllable to this extent, in accordance with the present invention, is comprised of a water jet of controlled speed and orifice diameter with a water flow that is tangentially applied to the epithelium, with the speed and flow rate being controlled by stagnation pressure to be sufficient to remove soft epithelium tissue, while washing it away, but insufficient to affect in any way the harder tissue of the Bowman's layer. Water of this speed and flow rate is simply shed off the Bowman's layer without other effect. More accurately stated, there can be some damage to the Bowman's layer but the time to begin to damage the Bowman's layer is generally much greater than the time to remove the epithelium. Thus, the procedure time is limited to avoid damaging the Bowman's layer.

The above objects and other features and advantages of the present invention will become more evident from the following discussion and drawings in which:

SHORT DESCRIPTION OF THE DRAWINGS

FIG. 1 is a side section view of an eye showing the corneal layers of epithelium and Bowman's layer;

FIG. 2 is a side schematic view of the device of the present invention being applied to and used to remove the epithelium layer;

Figure 4:
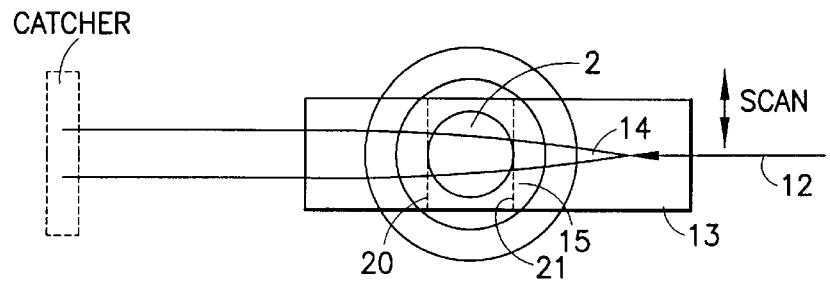
Figure 5:
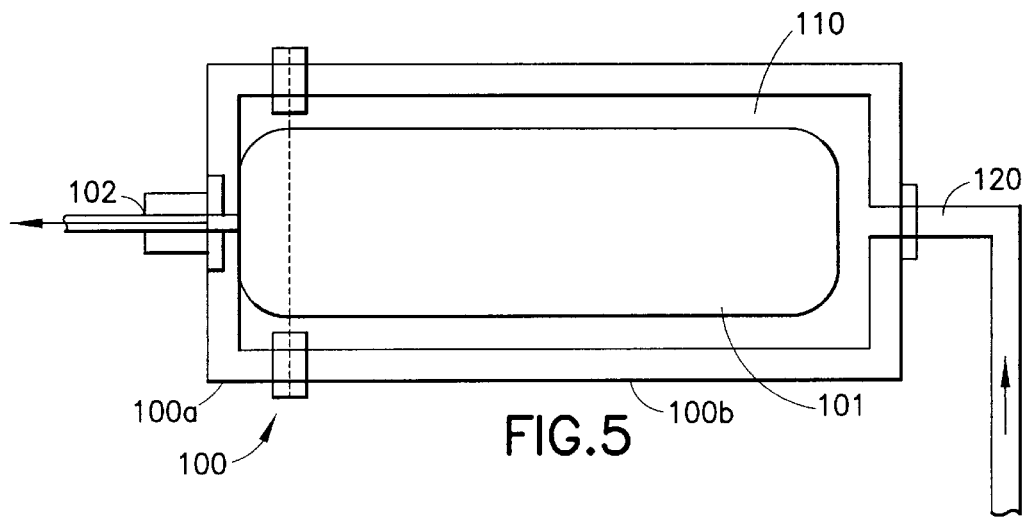
Figure 6:
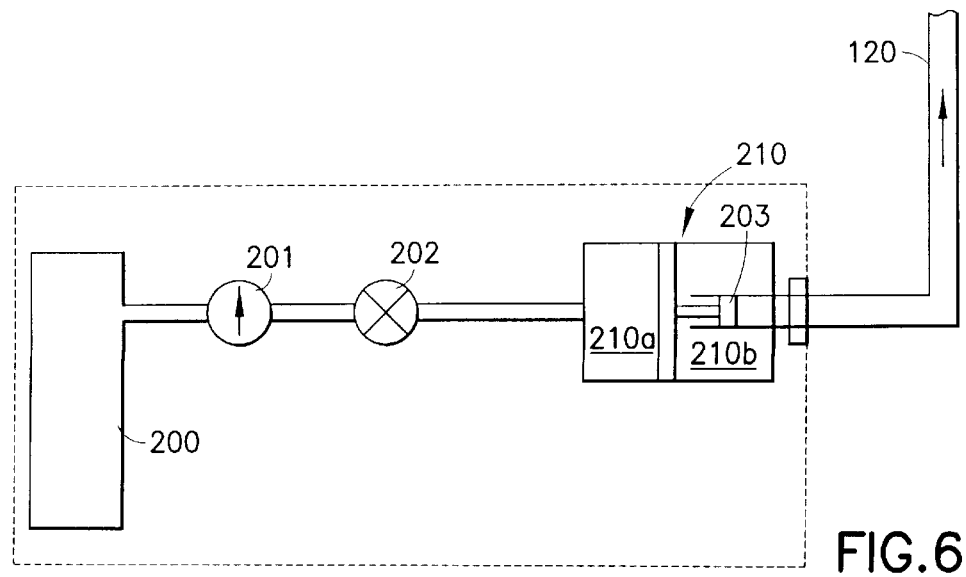

FIG. 3 is a bottom view of the applanating plate shown in FIG. 2 taken alone line 3—3, with schematic indication of the formation of a sheet waterjet beam, FIG. 4 is a top view through the transparent plate being applied to the cornea taken along line 4—4 of FIG. 2, with masked areas being shown, FIG. 5 is a schematic cross section view of a preferred device with a pressurizing handle used in providing the pressurized waterjet, from a replaceable compressed container (in the handle) which is converted to the waterjet sheet beam, and FIG. 6 is a schematic view of a foot pedal control for the working pressure being transmitted to the pressurizing handle shown in FIG. 5.

DETAILED DESCRIPTION OF THE INVENTION

In accordance with the present invention, the method for selectively removing epithelium material from the cornea with a water jet preferably comprises the steps of:

i) converting a high speed water jet to a sheet water jet beam, flowing along the surface of a plate with conversion means (conversion to the sheet water beam usually results in a drop in the force of the water jet (out pressure, i.e., stagnation pressure);

ii) providing the sheet water jet beam with a stagnation pressure or speed sufficient to remove epithelium tissue but of a speed and flow rate and time of the process insufficient to affect the Bowman's layer;

iii) causing the sheet water jet beam to tangentially contact the epithelium layer, while the cornea is lightly applanated to thereby remove all or a selected portion thereof.

In a preferred embodiment, masking means is utilized to mask off any portion of the epithelium, which is not to be removed, prior to effecting epithelium removal. It is also preferred that with a sheet water jet of smaller cross section width than that of the area of the epithelium material to be removed, means are provided for permitting lateral movement thereof in a brushing-like motion to ensure that the water jet sheet contacts and removes all of the epithelium material which is to be removed.

While water jets have been used in the past, e.g. U.S. Pat. No. 3,818,913 issued to Michael Wallach, to disintegrate cataracts, the effectiveness of those procedures has been based on the hardness of the material to be disintegrated, i.e., the hard cataracts are emulsified while surrounding soft tissue is unaffected. This is a result of a concentrated jet which is directed normal to the plane of the cataract. Operation of the sheet water jet beam of the present invention is diametrically opposed, with removal of the softer material (epithelium layer) while the harder material remains unaffected), resulting from directing of a controlled pressure waterjet in a direction tangential to the tissue to be removed.

In accordance with the present invention the device comprises:

a) means for dispensing a controllable circular or other section high speed, water-jet, with a nozzle orifice of specific diameter (the nozzle orifice diameter determines a constant rate for the fluid flow), and b) means for laterally radiating the water jet into a sheet waterjet beam having sufficient speed and flow rate to remove epithelium layer material within a specific time window but at a speed and flow rate less than that which affects tissue material of the underlying Bowman's layer, and c) means for tangentially directing the sheet waterjet beam against the epithelium layer which is to be removed.

In a preferred embodiment, the means for laterally radiating the water jet into the sheet waterjet beam comprises a preferably flat, impinging surface, e.g., a smooth transparent glass or polycarbonate applanting plate similar to a microscope slide, adapted to be adjacently placed relative to the epithelium surface (usually parallel to the cornea). In operation, a circular waterjet of sterile water or balanced salt solution or other related fluid of predetermined pressure and flow rate orifice diameter is directed to the surface of the plate, which is adjacent the epithelium surface, with a small incident angle, preferably about 15°. Thus, for example, a waterjet at a pressure of 4000–6000 psi emanating from a waterjet orifice of 100 μm, when made incident on a flat glass plate with a 15° angle of incidence, becomes a narrow sheet beam hugging the surface of the glass with a width of from about 1–2 mm. Variations in stagnation psi, orifice diameter, angle of incidence, distance from the point of impinge went to the cornea and frictional coefficient of the plate will controllably vary the size of the sheet beam as well as the force exerted thereby. The narrow sheet beam hugs the plate and the plate is placed closely adjacent the anterior surface of the cornea (i.e., adjacent and tangential to the epithelium thereof) with the plate-hugging water providing a slight separation between the plate and the cornea. The force of the plate on the cornea, about 2 grams wt., applanates the cornea to a circular diameter of about 5 mm. The sheet water beam acts as a narrow, flat, linear brush moving in the direction of the water with "brushed" epithelial tissue being carried away with the water flow. To effect removal of epithelial tissue, lateral to the sheet beam, the narrow beam is manually scanned from one side to the other side. Removal of the epithelial tissue requires about 5–6 seconds with additional "brushing" time simply irrigating the eye without affecting other corneal tissue up to a time of 15 seconds. To avoid excessive time and possible effect on other corneal tissue, the water or fluid flow is made to stop automatically in about 8 seconds. This is determined by the volume of the sterile water or balanced salt solution initially made available for the procedure.

Three parameters involved in the present invention are:

1) the speed of the water or other sterile fluid which encounters the cornea (determined by the stagnation pressure and the distance along the plate that the water flows before encountering the corneal tissue);

2) the flow rate (determined by the nozzle orifice diameter and the stagnation pressure and is constant along the beam), and 3) the duration time of application of the water to the cornea (determined by initial volume of water made available for the procedure).

A replaceable sterile, plastic container containing sterile balanced salt solution (BSS) with a typical volume of about 15 ml is used as a reservoir for the sheet beam. The container, has flexible walls (e.g., of flexible plastic), and is pressurized by applying high pressure water (or other working fluid) around the container which is contained in a pressure volume comprising the device handle. The high pressure fluid, which need not be sterile, enters the handle through a small diameter, flexible tubing and compresses the plastic container such that the sterile fluid within attains the same pressure as the working fluid with the sterile fluid being expelled through a nozzle of predetermined diameter which controls the flow rate. Preferably a manual (or foot controlled) hydraulic line system provides the pressure for the working fluid.

Alternatively, the flexible plastic container or bottle is placed in a high pressure chamber associated with the pump and the sterile fluid leaving the bottle goes to the device through the flexible tubing. A further refinement is to use a flexible membrane to isolate the plastic bottle from the high pressure fluid. This also provides a further barrier to any possible cross contamination.

If only a segment of the epithelium layer is to be removed, the portion which is to remain is masked off prior to and during the "brushing" and the sheet water beam does not remove any epithelial tissue under the mask. The shape of the mask is typically circular but other shapes are possible, as appropriate.

A selective pressure sufficient to cut epithelium tissue but not tissue of the Bowman's layer has been discovered to range from about 4000 to 6000 psi, with water jet diameters ranging from 60 to 100 $\mu$m in time periods up to about 8 seconds. It is understood that it is the water jet speed and flow rate of the sheet beam (stagnation psi) which is the determinative factor regarding epithelium tissue removal without effect on the Bowman's layer and not the speed as it issues from the waterjet source, since frictional forces reduce the pressure by a measurably determinative degree. It is also understood that a water beam which is not made into a sheet, but which is properly directed and scanned, with the appropriate pressure and force is similarly operable. Though not as desirable, non-planar plates may be utilized to provide the directed and widened water jet beam.

DETAILED DESCRIPTION OF THE DRAWINGS AND THE PREFERRED EMBODIMENT

With reference to the drawings, in FIG. 1, cornea 1 of eye 10 is shown in partial cross section to indicate the outer epithelium layer 2 of the cornea of about 40–50 $\mu$m thickness, beneath which is the thinner (about 15 microns) and harder Bowman's layer 3. Since the cornea is the visual gateway to the eye, disorders of the epithelium adversely affect vision. However because of the regenerative nature of the epithelium, treatment of the epithelium is most efficacious by simple removal of the epithelium layer and then letting it regenerate. The underlying Bowman's layer 3 is not however similarly regenerative and it must not be damaged or removed during removal of the epithelium layer. The epithelium grows best and fastest over the surface of an undamaged Bowman's layer. The device 11, as shown in FIG. 2, for removing the epithelium layer 2, without affecting the Bowman's layer 3, comprises a source for a circular diameter waterjet beam 12 of controlled speed, flow rate and flow time. The waterjet beam 12 is directed to strike applanating plate 13 at small angle $\alpha$ (which is about 15°). The beam 12 widens, as shown in FIGS. 3 and 4, to form sheet beam 14, with the velocity thereof keeping it in contact with plate 13. Plate 13 is tangentially positioned adjacent the epithelium layer 2 to be removed with that region between target lines 20 and 21 (shown in FIG. 4), with the waterjet sheet beam 14 contacting and removing the epithelium layer which is exposed by protective mask 15. The frictional contact with the plate 13 causes the sheet beam 14, at its point of contact with the epithelium layer, to be within the speed and flow rate to remove the epithelium layer but less than that required to affect the Bowman's layer 3. As indicated by the arrows in FIGS. 3 and 4, the beam sheet 14 is laterally scanned, as required, along the applanating plate 13, to ensure complete lateral removal of the epithelium layer 2, with a brush-like motion. The entire procedure takes about 5 seconds and any residual water of the water jet beam, washes away residual epithelial tissue and simply irrigates the Bowman's layer without otherwise affecting it.

An elegantly simple but positively controlled device for providing the waterjet beam is shown in FIG. 5, wherein handle 100, controlled by the surgeon provides an interior pressure volume 110 into which discardable flexible container 101 is inserted (interfaced threaded engagement of handle elements 100a and 100b) permits opening and closing of the handle for insertion access of the flexible container 101. The container is sized to contain sterile fluid which lasts only about 8 seconds (as predetermined) when the sterile fluid is expelled through nozzle orifice 102 (of predetermined diameter). With a compressed pressure of about 4000–6000 psi, the flexible container is generally of a volume of 15 ml for an operable stagnation pressure to effect epithelium removal.

Hydraulic fluid pressure is made to enter volume 110 from flexible conduit 120, which, as shown in FIG. 6, is effected and controlled by a foot pedal. Pressure from high pressure gas storage bottle 200 is controllably released through regulator (inlet and outlet gauge 201) and on/off control valve 202 to drive piston 203 contained in intensifier 210. Chambers 210a and 210b contain gas at predetermined pressures, whereby when chamber 210a is pressurized by activation of the gas pressure from bottle 200, piston 203 drives fully enclosed fluid (e.g., water) through flexible conduit 120 to effect the container pressurization. Release of pressure in chamber 210a, permits the gas chamber 210b to reset the piston. Continued pressure on piston 203 continues constant pressure until the fluid in container 101 is exhausted and the operator releases pressurization. The waterjet source shown in FIGS. 5 and 6, while useful in the present method and for use with the device of the present invention, is also useful in other operative uses of pressurized waterjets requiring control flow.

It is understood that the above discussion and drawings are illustrative of the present invention and that changes in device structure and method of operation is possible without departing from the scope of the present invention as defined by the following claims:

What is claimed is:

1. A method for selectively removing selected epithelium material from an epithelium layer of a cornea of an eye comprising the steps of:

i) providing a waterjet beam with a speed and flow rate so that within a specific time it is sufficient to remove epithelium tissue but of a speed and flow rate insufficient to affect a Bowman's layer;

ii) causing the waterjet beam to tangentially contact the epithelium layer and to thereby remove a selected portion thereof wherein a planar plate is positioned adjacent to and tangential to the epithelium layer of the cornea whereby waterjet beam contacts the planar plate and is converted to a waterjet beam, in the form of a sheet which removes the epithelium material.

2. The method of claim 1, wherein a portion of epithelium matter which is not selected for removal is masked prior to the tangential contact of the waterjet beam with the epithelium layer.

3. The method of claim 1, wherein the planar plate, adjacent to and tangential to the epithelium layer, is made to contact and applanate the cornea.

4. The method of claim 1 wherein the sheet waterjet beam is laterally scanned relative to the epithelium layer.

5. The method of claim 1, wherein the speed and flow rate sufficient to remove epithelium tissue but of the speed and flow rate insufficient to affect a Bowman's layer ranges between 4000 to 6000 psi, with waterjet diameters ranging from 60 to 100 $\mu$m and an application time of less than 8 seconds.

6. A device for selective removal of epithelium material from the cornea of an eye, said device comprising:
   a) means for dispensing a controllable high speed, waterjet,
   b) means for laterally radiating circular cross sectioned waterjet into a sheet waterjet beam having sufficient speed and flow rate to remove epithelium layer material, but at a speed and flow rate less than that which affects tissue material of a Bowman's layer below the epithelium material, and
   c) means for tangentially directing the sheet waterjet beam against the epithelium layer which is to be removed wherein the means for laterally radiating the water jet into the sheet waterjet beam comprises a plate positioned adjacent to and tangential to the epithelium layer of the cornea whereby the waterjet of circular cross section contacts the plate and is converted into the sheet waterjet beam which in turn is tangentially directed against the epithelium layer to remove the epithelium material.

7. The device of claim 6, wherein the device further comprises masking means which prevents removal of epithelium tissue which is not selected for removal.

8. A device for the controlled release of a pressurized waterjet for use in controlled cutting of eye tissue, comprising:
   a) manually controlled handle means having a pressurizable volume therein and a nozzle orifice of a predetermined open cross section, said handle means being controlled by the manual movement thereof;
   b) means for containing a flexible compressible container within said pressurizable volume, with said container containing a predetermined volume of sterile fluid, said container, when positioned in said pressurizable volume having an opening aligned with said nozzle orifice;
   c) pressurizing means for pressurizing the pressurizable volume thereby controllably compressing said flexible compressible container whereby the sterile fluid in the container is expelled through the opening of the container and out of the nozzle orifice as a waterjet of pre-determined speed and flow rate; and
   d) means for laterally radiating said waterjet into a sheet waterjet beam having a sufficient speed and flow rate to permit cutting of a desired portion of said eye tissue without damaging a remaining uncut portion of said eye tissue.

9. The device of claim 8, wherein the pressurizing means comprises an operator controlled hydraulic pump system.

* * * * *